United States Patent
Gunaratnam et al.

(10) Patent No.: US 9,132,256 B2
(45) Date of Patent: Sep. 15, 2015

(54) CONNECTOR FOR A RESPIRATORY MASK AND A RESPIRATORY MASK

(71) Applicant: ResMed Limited, Bella Vista (AU)

(72) Inventors: Michael Kassipillai Gunaratnam, Marsfield (AU); Joanne Elizabeth Drew, Balgowlah Heights (AU); Geoffrey Crumblin, Baulkham Hills (AU); Philip James Jenkinson, Chittaway Point (AU); Susan Robyn Lynch, Bella Vista (AU)

(73) Assignee: ResMed Limited, Bella Vista (AU)

( * ) Notice: Subject to any disclaimer, the term of this patent is extended or adjusted under 35 U.S.C. 154(b) by 0 days.

(21) Appl. No.: 13/871,375

(22) Filed: Apr. 26, 2013

(65) Prior Publication Data

US 2013/0233317 A1    Sep. 12, 2013

Related U.S. Application Data

(63) Continuation of application No. 13/137,524, filed on Aug. 24, 2011, now Pat. No. 8,439,039, which is a continuation of application No. 12/382,597, filed on Mar. 19, 2009, now Pat. No. 8,011,369, which is a (Continued)

(30) Foreign Application Priority Data

Jun. 18, 1999   (AU) .................................... PQ1029

(51) Int. Cl.
*A62B 18/02* (2006.01)
*A61M 16/08* (2006.01)
(Continued)

(52) U.S. Cl.
CPC ....... *A61M 16/0816* (2013.01); *A61M 16/0066* (2013.01); *A61M 16/06* (2013.01);
(Continued)

(58) Field of Classification Search
CPC ............ A61M 16/00; A61M 16/0875; A61M 16/208; A61M 39/1011; A61M 39/391012; A61M 39/1055; A61M 2039/1033; A62B 18/00
USPC ............. 128/202.27, 205.25, 206.21, 206.28, 128/207.12, 207.13, 207.18
See application file for complete search history.

(56) References Cited

U.S. PATENT DOCUMENTS

| 2,029,129 A | 1/1936 | Schwartz |
| 2,112,213 A | 3/1938 | Schwartz |

(Continued)

FOREIGN PATENT DOCUMENTS

| CA | 1039144 | 9/1978 |
| DE | 197 57 703 C1 | 10/1999 |

(Continued)

OTHER PUBLICATIONS

English Translation of Japanese Office Action for Appln. No. 2001-504441, mailed Oct. 26, 2004, 6 pgs.

(Continued)

*Primary Examiner* — Kristen Matter
(74) *Attorney, Agent, or Firm* — Nixon & Vanderhye P.C.

(57) ABSTRACT

A respiratory mask assembly for delivering breathable gas to a patient includes a frame and an elbow assembly. The frame has a front surface and a rear surface adapted in use to face the patient. The frame includes a main body providing an aperture therethrough for the introduction of breathable gas into a nasal breathing cavity. The elbow assembly is swivelably coupled to the front surface of the frame. The elbow assembly includes a swivel elbow that defines an intake port and an exhaust port separated from the intake port using a baffle. The elbow assembly includes an end portion that interfaces with the aperture of the frame.

32 Claims, 9 Drawing Sheets

Related U.S. Application Data continuation of application No. 11/362,722, filed on Feb. 28, 2006, now Pat. No. 7,523,753, which is a continuation of application No. 10/636,588, filed on Aug. 8, 2003, now Pat. No. 7,066,178, which is a continuation of application No. 09/594,775, filed on Jun. 16, 2000, now Pat. No. 6,691,707.

(51) Int. Cl.
  *A61M 16/06* (2006.01)
  *A61M 16/00* (2006.01)

(52) U.S. Cl.
  CPC ....... *A61M16/0616* (2013.01); *A61M 16/0622* (2013.01); *A61M 16/0633* (2013.01); *A61M 16/0638* (2013.01); *A61M 16/0683* (2013.01); *A61M 16/08* (2013.01); *A61M 16/0875* (2013.01); *A61M 2205/42* (2013.01); *A61M 2206/14* (2013.01)

(56) References Cited

U.S. PATENT DOCUMENTS

| | | |
|---|---|---|
| 2,295,296 A | 9/1942 | Schmidt |
| 2,381,568 A | 8/1945 | Booharin |
| 2,931,356 A | 4/1960 | Schwarz |
| 4,015,598 A | 4/1977 | Brown |
| 4,463,755 A | 8/1984 | Suzuki |
| 4,794,921 A | 1/1989 | Lindkvist |
| 4,919,128 A | 4/1990 | Kopala et al. |
| 4,974,586 A | 12/1990 | Wandel et al. |
| 5,018,519 A | 5/1991 | Brown |
| 5,322,059 A | 6/1994 | Walther |
| 5,560,354 A | 10/1996 | Berthon-Jones et al. |
| 5,694,922 A | 12/1997 | Palmer |
| 5,871,011 A | 2/1999 | Howell et al. |
| 5,918,598 A | 7/1999 | Belfer et al. |
| 5,921,239 A | 7/1999 | McCall et al. |
| 5,937,851 A | 8/1999 | Serowski et al. |
| 5,975,077 A | 11/1999 | Hofstetter et al. |
| 6,119,693 A | 9/2000 | Kwok et al. |
| 6,196,223 B1 | 3/2001 | Belfer et al. |
| 6,374,826 B1 | 4/2002 | Gunaratnam et al. |
| 6,532,961 B1 | 3/2003 | Kwok et al. |
| 6,691,707 B1 | 2/2004 | Gunaratnam et al. |
| 6,907,882 B2 | 6/2005 | Ging et al. |
| 7,047,972 B2 | 5/2006 | Ging et al. |
| 7,066,178 B2 | 6/2006 | Gunaratnam et al. |
| 7,290,546 B2 | 11/2007 | Sprinkle et al. |
| 7,341,060 B2 | 3/2008 | Ging et al. |
| 7,487,772 B2 | 2/2009 | Ging et al. |
| 7,523,753 B2 | 4/2009 | Gunaratnam et al. |
| 7,597,100 B2 | 10/2009 | Ging et al. |
| 7,743,767 B2 | 6/2010 | Ging et al. |
| 7,874,291 B2 | 1/2011 | Ging et al. |
| 7,938,116 B2 | 5/2011 | Ging et al. |
| 7,997,267 B2 | 8/2011 | Ging et al. |
| 8,011,369 B2 | 9/2011 | Gunaratnam et al. |
| 8,025,057 B2 | 9/2011 | Ging et al. |
| 8,371,302 B2 | 2/2013 | Ging et al. |
| 8,387,616 B2 | 3/2013 | Ging et al. |
| 8,479,736 B2 | 7/2013 | Ging et al. |
| 2001/0032648 A1 | 10/2001 | Jestrabek-Hart |
| 2004/0025881 A1 | 2/2004 | Gunaratnam et al. |
| 2009/0194112 A1 | 8/2009 | Gunaratnam et al. |
| 2012/0048276 A1 | 3/2012 | Gunaratnam et al. |
| 2013/0146059 A1 | 6/2013 | Ging et al. |
| 2013/0174839 A1 | 7/2013 | Ging et al. |
| 2013/0291870 A1 | 11/2013 | Ging et al. |

FOREIGN PATENT DOCUMENTS

| | | |
|---|---|---|
| JP | 57-190568 | 11/1982 |
| JP | 61-52707 | 11/1986 |
| JP | 9-10311 | 1/1997 |
| JP | 3745684 | 12/2005 |
| WO | WO 98/34665 | 8/1998 |
| WO | WO 98/48878 | 11/1998 |

OTHER PUBLICATIONS

Office Action issued in Japanese Appln. No. 2005-276300 (Jun. 8, 2010) w/English translation.

Office Action issued in a related Japanese Application No. 2010-273418 (Jun. 12, 2012) with English translation.

Final Office Action issued a corresponding Japanese Application No. 2010-273418 (Dec. 4, 2012) with English translation thereof.

CONNECTOR FOR A RESPIRATORY MASK AND A RESPIRATORY MASK

This application is a continuation of U.S. patent application Ser. No. 13/137,524, filed Aug. 24, 2011, now U.S. Pat. No. 8,439,039, which is a continuation of U.S. patent application Ser. No. 12/382,597, filed Mar. 19, 2009, now U.S. Pat. No. 8,011,369, which is a continuation of U.S. patent application Ser. No. 11/362,722, filed Feb. 28, 2006, now U.S. Pat. No. 7,523,753, which is a continuation of U.S. patent application Ser. No. 10/636,588, filed Aug. 8, 2003, now U.S. Pat. No. 7,066,178, which is a continuation of U.S. patent application Ser. No. 09/594,775, filed Jun. 16, 2000, now U.S. Pat. No. 6,691,707, which claims priority to Australian Application No. PQ 1029, filed Jun. 18, 1999, each of which is incorporated herein by reference in its entirety.

BACKGROUND OF THE INVENTION

1. Field of Invention

The present invention relates to a connector for a respiratory mask and a respiratory mask.

The invention has been developed primarily for use with a breathable gas supply apparatus in Continuous Positive Airway Pressure (CPAP) treatment of, for example, Obstructive Sleep Apnea (OSA) and other ventilatory assistance treatments, such as Non Invasive Positive Pressure Ventilation (NIPPV) and will be described hereinafter with reference to these applications. However, it will be appreciated that the invention is not limited to these particular fields of use and also finds application in, for example, assisted respiration, mechanical ventilation and the like.

2. General Background and Related Art

CPAP treatment is a common ameliorative treatment for breathing disorders including OSA. CPAP treatment, as described in U.S. Pat. No. 4,944,310, provides pressurized air or other breathable gas to the entrance of a patient's airways at a pressure elevated above atmospheric pressure, typically in the range 3-20 cm $H_2O$.

It is also known for the level of treatment pressure to vary during a period of treatment in accordance with patient need, that form of CPAP being known as automatically adjusting nasal CPAP treatment, as described in U.S. Pat. No. 5,245,995.

NIPPV is another form of treatment for breathing disorders which can involve a relatively higher pressure of gas being provided in the patient mask during the inspiratory phase of respiration and a relatively lower pressure or atmospheric pressure being provided in the patient mask during the expiratory phase of respiration.

In other NIPPV modes, the pressure can be made to vary in a complex manner throughout the respiratory cycle. For example, the pressure at the mask during inspiration or expiration can be varied through the period of treatment, as disclosed in the applicant's international PCT patent application No. PCT/AU97/00631.

Typically, the ventilatory assistance for CPAP or NIPPV treatment is delivered to the patient by way of a respiratory, preferably nasal, mask. Alternatively, a mouth mask or full face mask can be used. In this specification any reference to a mask is to be understood as incorporating a reference to a nasal mask, mouth mask or full face mask, unless otherwise specifically indicated.

In this specification any reference to CPAP treatment is to be understood as embracing all of the above-described forms of ventilatory treatment or assistance.

Breathable gas supply apparatus broadly comprise a flow generator constituted by a continuous source of air or other breathable gas generally in the form of a blower driven by an electric motor. The electric motor driving the blower is typically controlled by a servo-controller under the control of a micro controller unit. A hospital piped supply can also be used. The gas supply is connected to a conduit or tube which, in turn, is connected to the patient's mask which incorporates, or has in close proximity, a gas washout vent for venting exhaled gases to the atmosphere. The gas washout vent is sometimes referred to as a $CO_2$ washout vent.

As CPAP and NIPPV treatments are normally administered while the patient is sleeping, minimization of the noise is desirable for both the comfort of the patient and any bed partner. The exhausting of exhaled gas to the atmosphere through the gas washout vent creates noise due to turbulence generated at a shear layer between the moving vented gases and the still atmospheric air.

It is also desirable to locate the vent as close as possible to the mask in a location which encourages a circulation of flow within the mask so as to eliminate exhaled $CO_2$ through the vent and encourage inhalation of the supplied breathable gas. In this way, the retention of $CO_2$ within the mask is minimized. Further, by increasing the venting efficiency in this manner, the overall gas outflow is minimized, thereby reducing the opportunity for noise production.

One approach to minimize the noise generated by the venting of the exhaled gas is to direct the gas along an exterior surface which is a smooth prolongation of an interior surface of the outlet of the gas washout vent. This reduces the interaction between the vented gas and the still atmospheric air and, thus, the noise generated.

An example of the above approach is the AeroClick vent produced by MAP which has an annular vent passage that directs the exhaled gases along an adjacent cylindrical section of equal exterior diameter to the interior diameter of the annular vent. The AeroClick vent suffers from several disadvantages. Firstly, the annular vent is incorporated into a swivel mechanism which requires a certain amount of play or clearance in order to rotate freely. This play allows the components forming the interior and exterior surfaces of the annular vent passage to become misaligned and the size of the vent outlet being decreased from optimum in some regions and increased from optimum in other regions. The decreased area regions increase by the velocity of the gas flowing therethrough which increases noise and can produce an unpleasant whistling effect. Secondly, the flow of the gas from the vent outlet to a state where its velocity is in substantial equilibrium with the atmosphere is interrupted by an external shoulder closely downstream of the vent outlet. The shoulder is provided to locate the gas supply conduit. The stresses in the flow caused by the shoulder lead to the generation of noise. Additionally, the flow path from the gas conduit into the vent outlet is not smooth which introduces discontinuities into the flow which result in further noise generation.

Further, the AeroClick vent and other prior art devices that are of a substantially cylindrical in-line configuration, the exhaled gas must thus be forced a relatively large distance (typically around 60 mm) before reaching the outlet to the atmosphere. This reduces $CO_2$ washout efficiency, as noted above, and requires additional patient effort to force the gas against the direction of flow coming from the flow generator.

It is an object of the present invention to substantially overcome or at least ameliorate the prior art disadvantages and, in particular, to reduce the noise generated by venting exhaled gases to the atmosphere.

SUMMARY OF THE INVENTION

Accordingly, in a first aspect, the present invention provides a connector comprising:

a mask end for connecting in fluid communication with the interior of a respiratory mask;

a supply conduit end disposed at an angle to the mask end for connecting in fluid communication with the outlet of a breathable gas supply conduit; and a gas washout vent passage having an inlet adjacent to, or forming part of, the mask end in fluid communication with the interior of the respiratory mask and an outlet in fluid communication with the atmosphere, the outlet including an interior surface that forms a smooth prolongation with an adjacent exterior surface of the connector, the vent outlet is disposed on the side of the connector remote the mask end, has a generally part-annular cross section and is adapted to direct the washout gas in a direction substantially perpendicular to the longitudinal axis of the mask end and substantially parallel to the longitudinal axis of the supply conduit end towards the supply conduit end.

The supply conduit end is preferably substantially perpendicular to the mask end. The supply conduit end can also be angled at approximately 135 degrees to the mask end.

Preferably, the connector includes a body portion and a cap portion, said body portion including said interior surface. The cap portion preferably also includes an interior surface spaced apart from the body portion interior surface, said body portion interior surface and said cap portion interior surface defining said vent passage therebetween.

The cap portion is desirably detachable from the body portion. The cap portion and body portion are also desirably rigid and fixed relative to each other when attached. The exterior of the body portion preferably includes grooves or ridges adapted to engage ridges or grooves respectively on the interior of the cap portion to attach the cap portion to the body portion. One of the body portion or cap portion preferably also includes a spacer extending between said cap portion interior surface and said body portion exterior surface.

In one form, the vent passage inlet is formed in the body portion adjacent to and downstream of the mask end, relative to the washout gas flow, and is in fluid communication with the mask interior via the body portion.

In another form, the vent passage inlet comprises part of the mask end and is in direct fluid communication with the mask interior.

The vent passage preferably comprises an inlet portion of relatively large cross-sectional area adjacent the vent passage inlet and an outlet portion of relatively small cross-sectional area adjacent the vent passage outlet.

The vent passage desirably comprises an inlet portion of constant cross-section, a relatively long outlet portion of constant cross-section and a relatively short transition portion of smoothly reducing cross-section extending from the inlet portion to the outlet portion. This shape reduces turbulence and affords a pressure drop from the interior of the mask to the outlet of the vent passage which reduces the pressure gradient at the outlet of the vent passage and, thus, reduces the noise generated.

The vent passage can also include internal ribs and/or an internal tortuous path to increase the pressure drop, if required.

The body portion is preferably of generally part toroidal shape. The cap portion is preferably of complimentary shape to a portion of the exterior of the body portion.

The vent passage preferably curves around the exterior of the body portion.

The connector desirably includes a swivel joiner at its supply conduit end, the exterior of the swivel joiner forming all, or a part, of said connector exterior surface.

In one form, the supply conduit end of the connector forms a smooth prolongation with the supply conduit. The supply conduit end and the supply conduit desirably have a substantially equal external diameter.

In another form, the swivel joiner forms a smooth prolongation with the supply conduit. The swivel joiner and the supply conduit having a substantially equal external diameter. The swivel joiner preferably includes an end of reduced external diameter adapted to be received within the interior of the supply conduit.

In a second aspect, the present invention provides a respiratory mask comprising:

a mask shell defining an interior of the respiratory mask;

a mask inlet for connecting in fluid communication with the outlet of a breathable gas supply conduit; and a gas washout vent passage having an inlet forming part of the mask shell and in fluid communication with the interior of the respiratory mask and an outlet in fluid communication with the atmosphere, the outlet including an interior surface that forms a smooth prolongation with an adjacent exterior surface of the mask shell, the vent outlet is disposed on the side of the mask remote the mask interior and is adapted to direct the washout gas in a direction substantially parallel to the longitudinal axis of the mask inlet and away from the mask inlet.

Preferably, the mask shell includes a body portion and a cap portion, said body portion including said interior surface. The cap portion preferably also includes an interior surface spaced apart from the body portion interior surface, said body portion interior surface and said cap portion interior surface defining said vent passage therebetween.

The cap portion is desirably detachable from the body portion. The cap portion and body portion are also desirably rigid and fixed relative to each other when attached. The exterior of the body portion preferably includes grooves or ridges adapted to engage ridges or grooves respectively on the interior of the cap portion to attach the cap portion to the body portion. One of the body portion or cap portion preferably also includes a spacer extending between the interior surface of the cap portion and the exterior surface of the body portion.

The vent passage preferably comprises an inlet portion of a relatively large cross-sectional area adjacent the vent passage inlet and an outlet portion of a relatively small cross-sectional area adjacent the vent passage outlet.

The vent passage desirably comprises a relatively long inlet portion of constant cross-section, a relatively long outlet portion of constant cross-section and a transition portion of smoothly reducing cross-section extending from the inlet portion to the outlet portion.

The vent passage preferably substantially follows the shape of the exterior of the body portion.

DETAILED DESCRIPTION OF THE PREFERRED EMBODIMENTS

Figure 1:
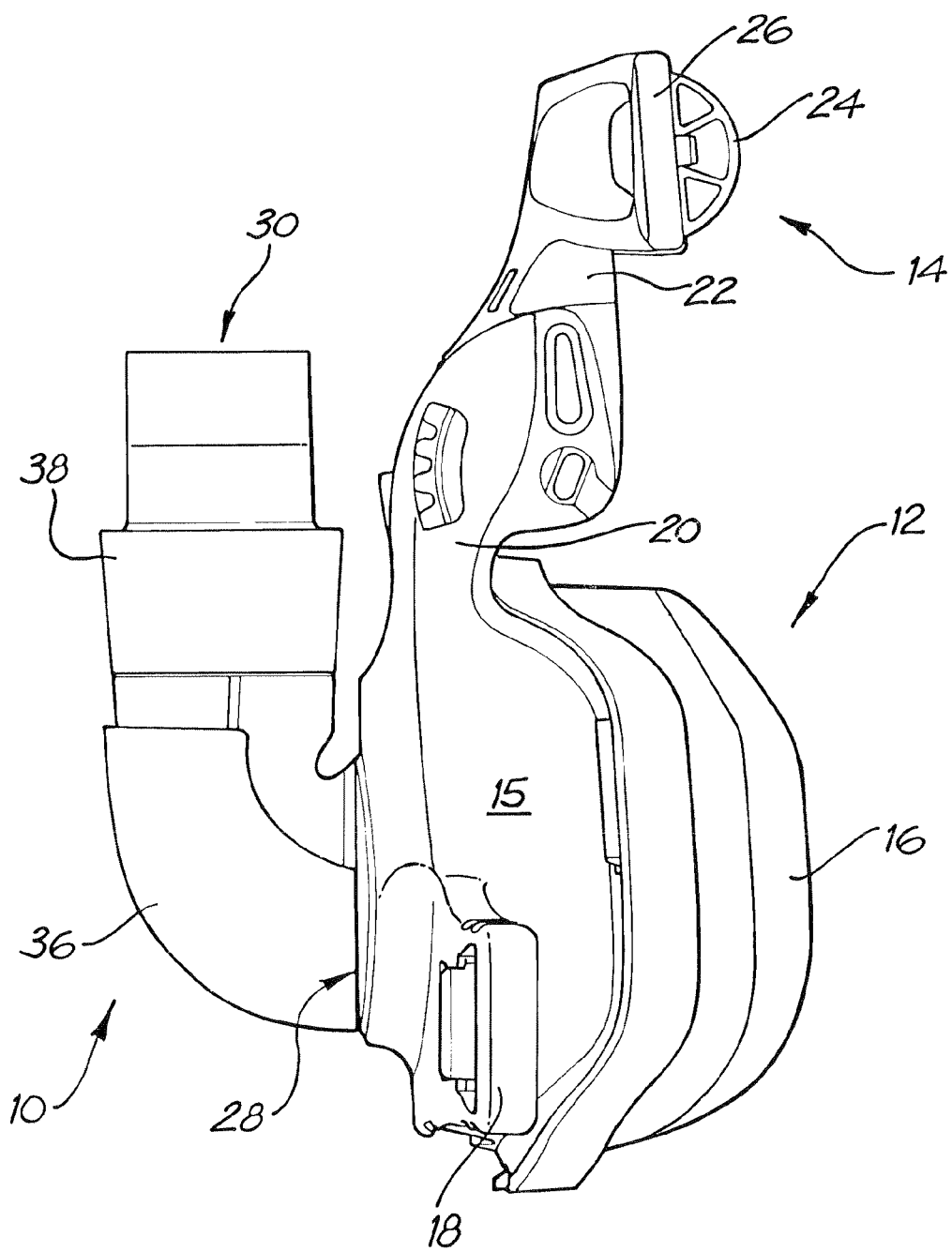
FIG. 1 is a side view of a first embodiment of a connector in accordance with the first aspect of the invention, shown attached to a nasal respiratory mask and forehead support.

FIGS. 1 to 5 show a first embodiment of the first aspect of the invention in the form of connector 10. The connector 10 is shown attached to a nasal respiratory mask 12 and forehead support device 14. The connector 10 is also suitable for use with a full face (i.e., nose and mouth) respiratory mask.

The mask 12 comprises a substantially rigid mask shell 15, a flexible mask cushion 16 and two slotted lower head strap connectors 18 (only one connector shown).

The forehead support device 14 includes a lower portion 20 which is pivotally mounted to an upper portion 22. The upper portion 22 includes forehead cushions 24 and two slotted upper head strap connectors 26 (only one cushion/connector shown).

Figure 2:
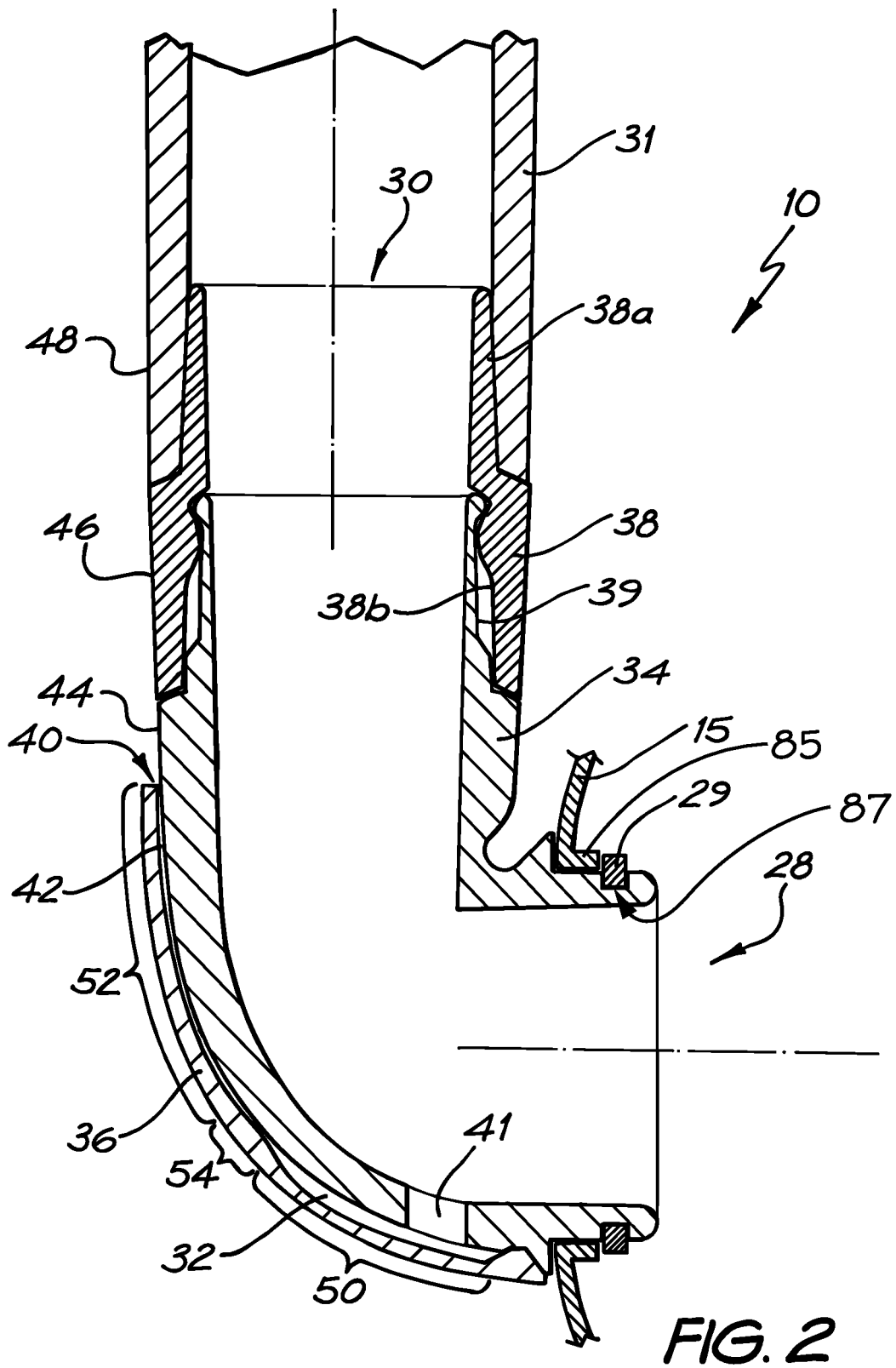
FIG. 2 is a cross-sectional side view of the connector shown in FIG. 1.

As best shown in FIG. 2, the connector 10 includes a mask end 28 for connecting in fluid communication with the interior of the respiratory mask 12 and a supply conduit end 30 disposed substantially perpendicularly to the mask end 28 for connecting in fluid communication with the outlet of a breathable gas supply conduit 31. The mask end 28 is rotatably coupled to the mask shell 15 by a retaining ring 29. As shown in FIG. 2, the mask shell 15 may include a flange 85 and the retaining ring 29 may be received in a receiving space (or groove) 87. The close proximity of the inlet ports 41, and the vent passage 32 overall, to the interior of the mask 12 advantageously increases $CO_2$ washout efficiency.

The connector 10 also includes a gas washout vent passage, indicated generally by the reference numeral 32, a body portion 34, a detachable cap portion 36 and a detachable swivel joiner 38. The conduit 31 is a non-rotatable friction push fit over end 38a of the swivel joiner 38. The end 38b of the swivel joiner 38 is a rotatable snap-engage fit with reduced diameter portion 39 of the body portion 34. The portion 39 is formed from resilient fingers to allow flexing during snap-engagement with the swivel joiner 38.

The vent passage 32 includes a pair of inlet ports 41 (see FIG. 4) formed in the body portion 34 of the connector 10 adjacent the mask end 28. The inlet ports 41 are in fluid communication with the interior of the mask 12 via the mask end 28. The vent passage 32 also includes an outlet 40 opening to the atmosphere. The outlet 40 includes an interior surface 42 (comprising an exterior surface of the body portion 34) that forms a smooth prolongation with an adjacent exterior surface 44 of the body portion 34. The smooth prolongation between the interior surface 42 and exterior surface 44 reduces noise by allowing the exhaled gases to vent along a continuous surface, as previously described. In order to minimize interruptions or disturbances that could generate turbulence downstream of the outlet 40, and thus noise, the adjacent exterior surfaces 46, 48 of the swivel joiner 38 and the gas supply conduit 31 respectively are also formed as smooth prolongations of the interior surface 42 and adjacent exterior surface 44.

Figure 3:
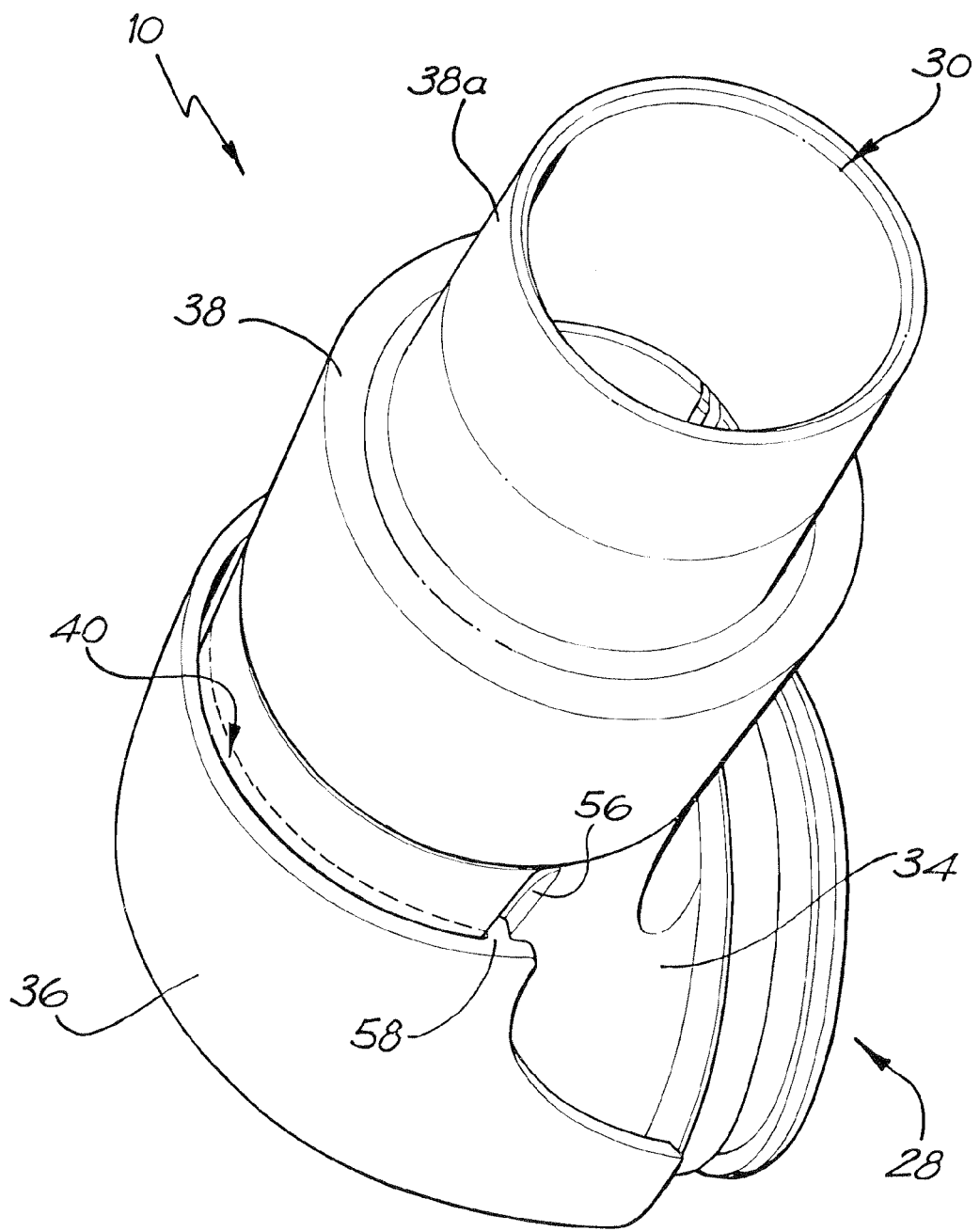
FIG. 3 is a perspective view of the connector shown in FIG. 1.

As best shown in FIG. 3, the vent passage outlet 40 is of generally part annular cross-section subtending an angle of approximately 180° and is located on the side of the connector 10 remote the mask end 28 and, thus, the mask 12. This ensures that gas is only vented along surfaces displaced, and facing away, from the mask 12 and the patient, which again minimizes the risk of the vented gases encountering noise-producing obstructions.

Returning to FIG. 2, it can be seen that the vent passage 32 comprises an inlet portion 50 of relatively large cross-sectional area compared to an outlet portion 52 of relatively small cross-sectional area. This provides a substantial pressure drop across the vent passage 32 and reduces the pressure drop between the outlet 40 and surrounding atmospheric air, again minimizing noise production. Also, the outlet portion 52 is relatively long in order to allow the gas to approach a laminar state and, thus, minimize turbulence before the gas exits to the atmosphere. A smooth tapering transition portion 54 is disposed between the inlet portion 50 and the outlet portion 52 which minimizes noise production by minimizing the introduction of any discontinuities into the gas flow.

Figure 4:
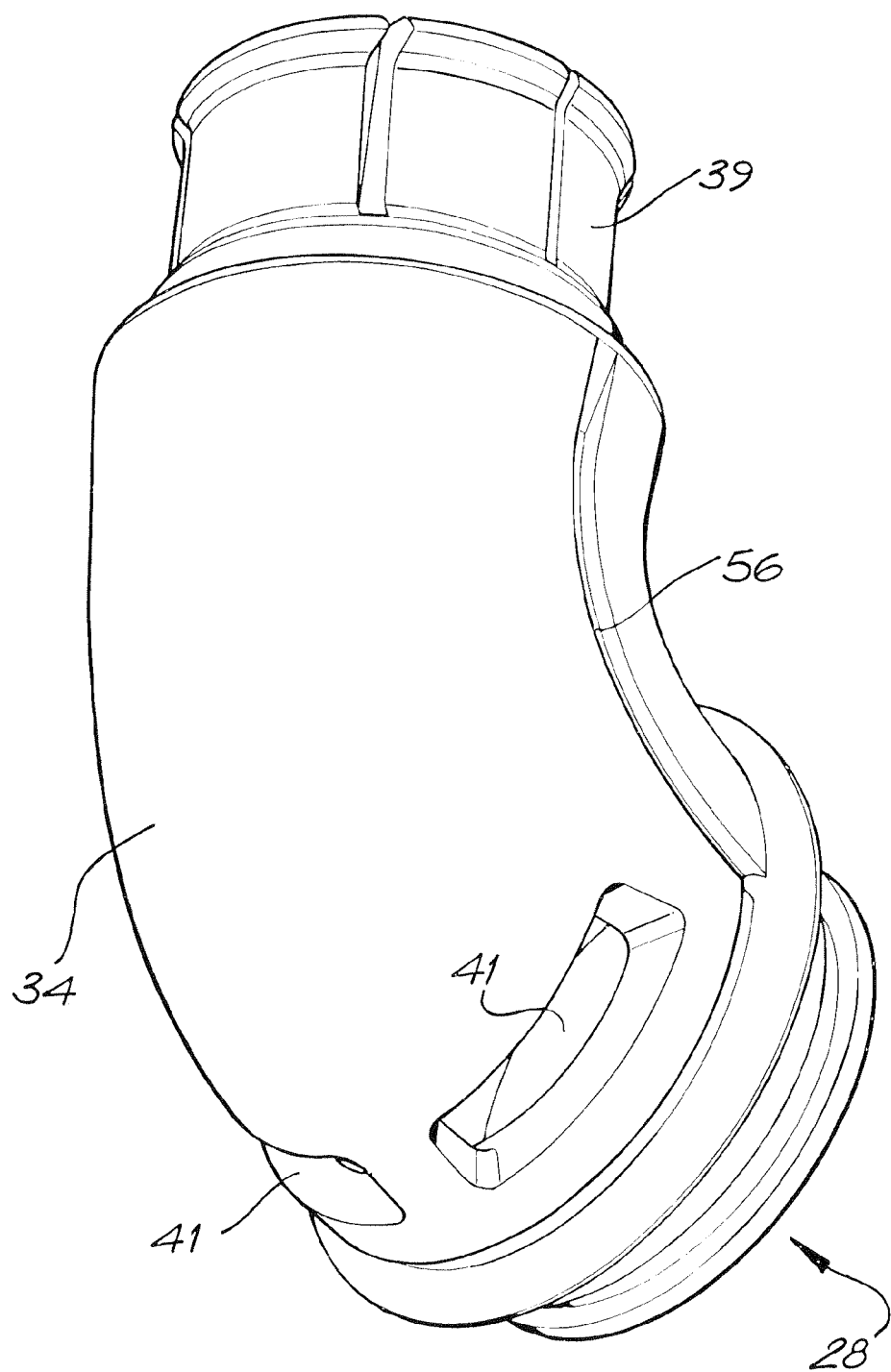
FIG. 4 is a perspective view of the connector shown in FIG. 1 with the cap portion removed.
Figure 5:
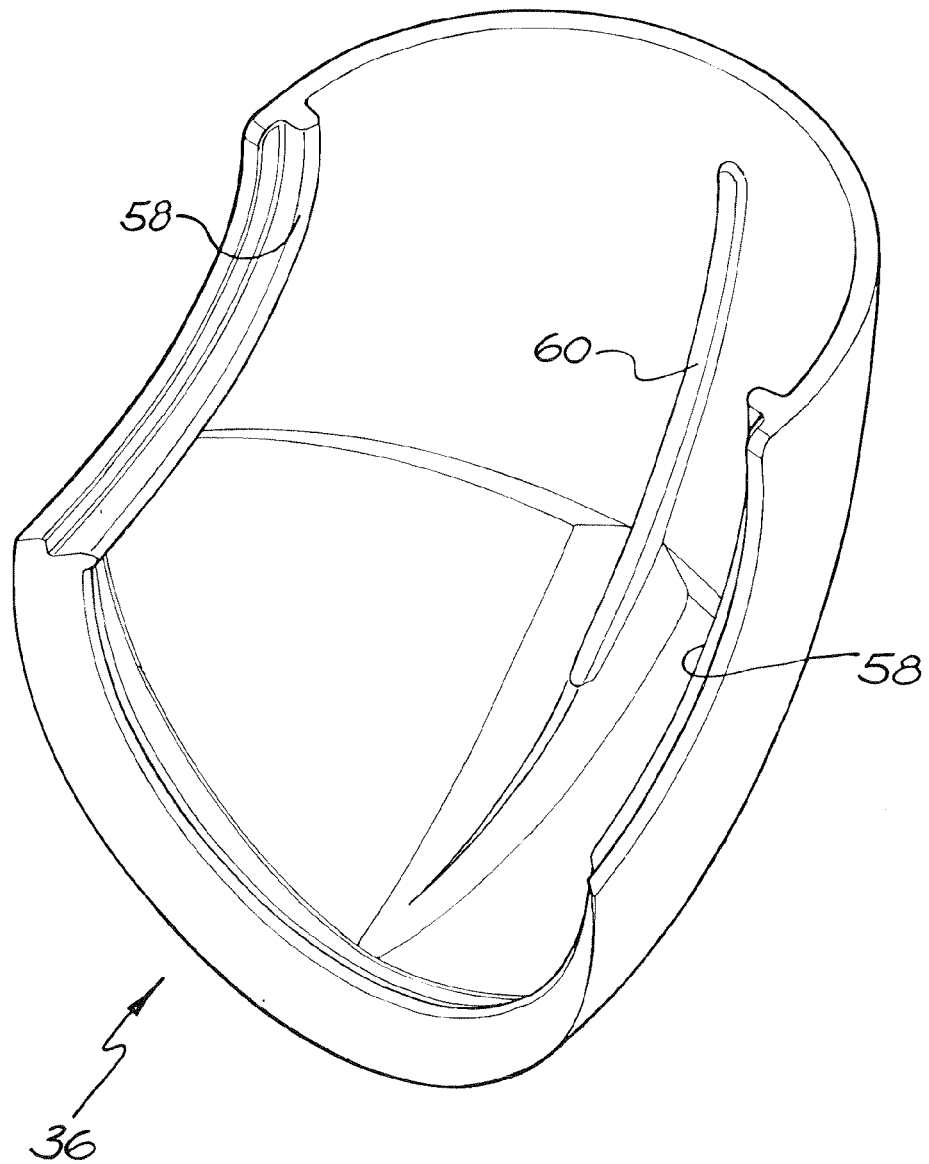
FIG. 5 is an underside perspective view of the cap portion of the connector shown in FIG. 1.

As best shown in FIGS. 3 and 4, the body portion 34 includes grooves 56 which are adapted to engage with ridges 58 provided on the cap portion 36 to allow the cap portion 36 to be manually attachable/detachable to/from the body portion 34 for ease of cleaning and replacement. As best shown in FIG. 5, the cap portion 36 also includes an interior strengthening rib 60 to provide rigidity and ensure the cross-sectional area of the vent passage 32 is not reduced due to external pressure, as may be caused by the patient rolling over onto their face during sleep. The detachable cap portion 36 also makes disassembly for cleaning easier and allows cap portions of various sizes to be used with a single body portion 34, thereby allowing the size and shape of the vent passage to be easily and quickly varied for particular treatment applications.

Although the connector 10 has been described with reference to the swivel joiner 38 being interposed between the connector 10 and the breathable gas supply conduit 31, it will be appreciated that the conduit can be joined directly to the body portion 34 if the ability to swivel is not required or if a swivel is provided elsewhere in the gas supply circuit. In that case, it is, of course, desirable for the external diameter of the gas supply conduit 31 to be equal to the adjacent external diameter of the exterior surface of the body portion 34.

Figure 6:
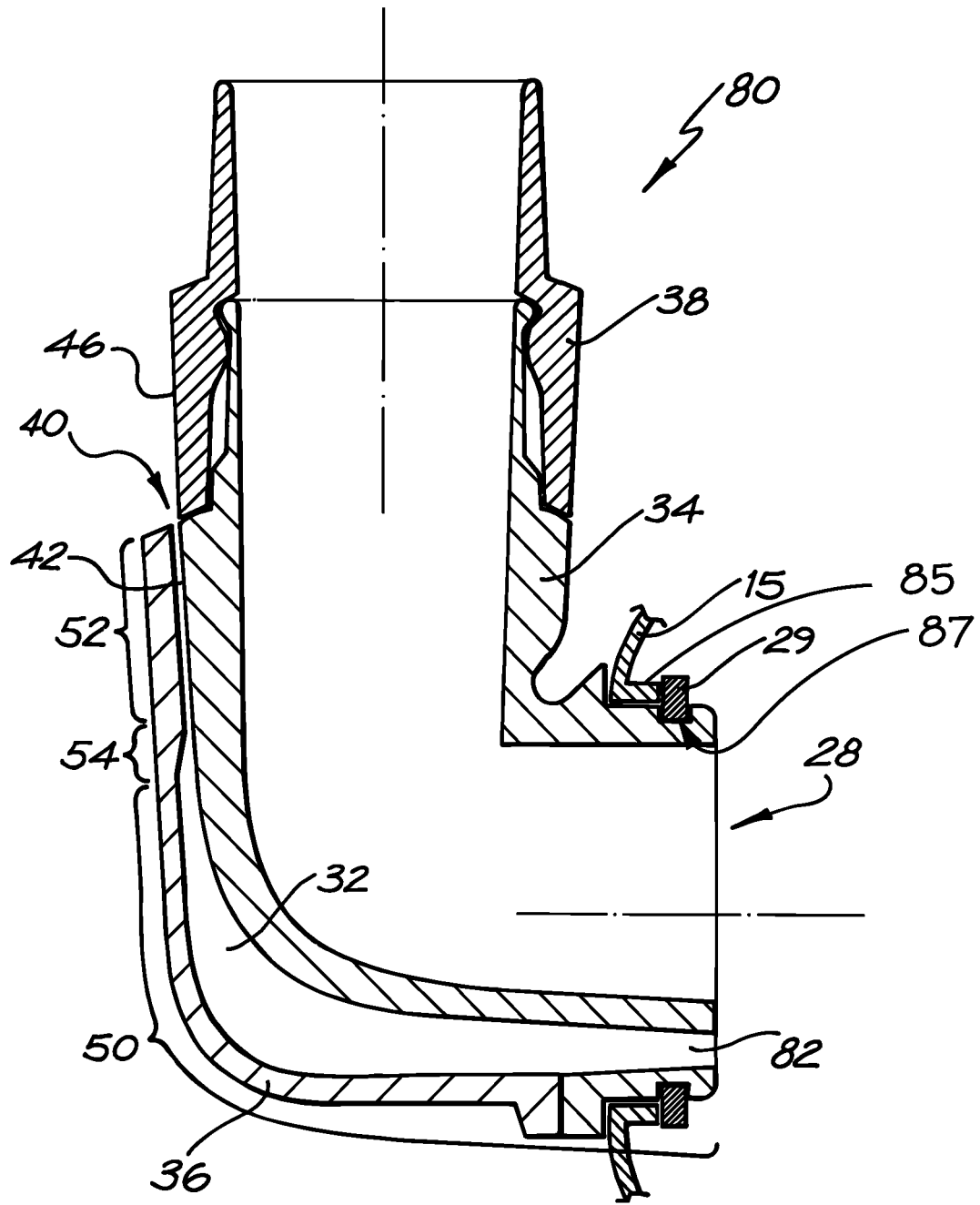
FIG. 6 is a cross-sectional side view of a second embodiment of a connector in accordance with the first aspect of the invention.

A second embodiment of connector 80 in accordance with the first aspect of the invention is shown in FIG. 6. Like reference numerals to those used in describing the first embodiment are used to indicate like features in the second embodiment.

The primary difference between the connector 10 and connector 80 is that the inlet ports 41 are omitted and an inlet port 82 of the gas washout vent passage 32 is incorporated into the mask end 28 of the connector 80. Thus providing direct fluid communication between the interior of the mask 12 and the vent passage 32 and further minimizing $CO_2$ retention. The inlet portion 50 of the vent passage 32 also provides a relatively long distance over which a gradual reduction in pressure can be achieved. Further, the interior surface of the vent passage outlet 40 forms a smooth prolongation with the adjacent exterior surface 46 of the swivel joiner 38 rather than the body portion 34, as with the first embodiment.

Figure 7:
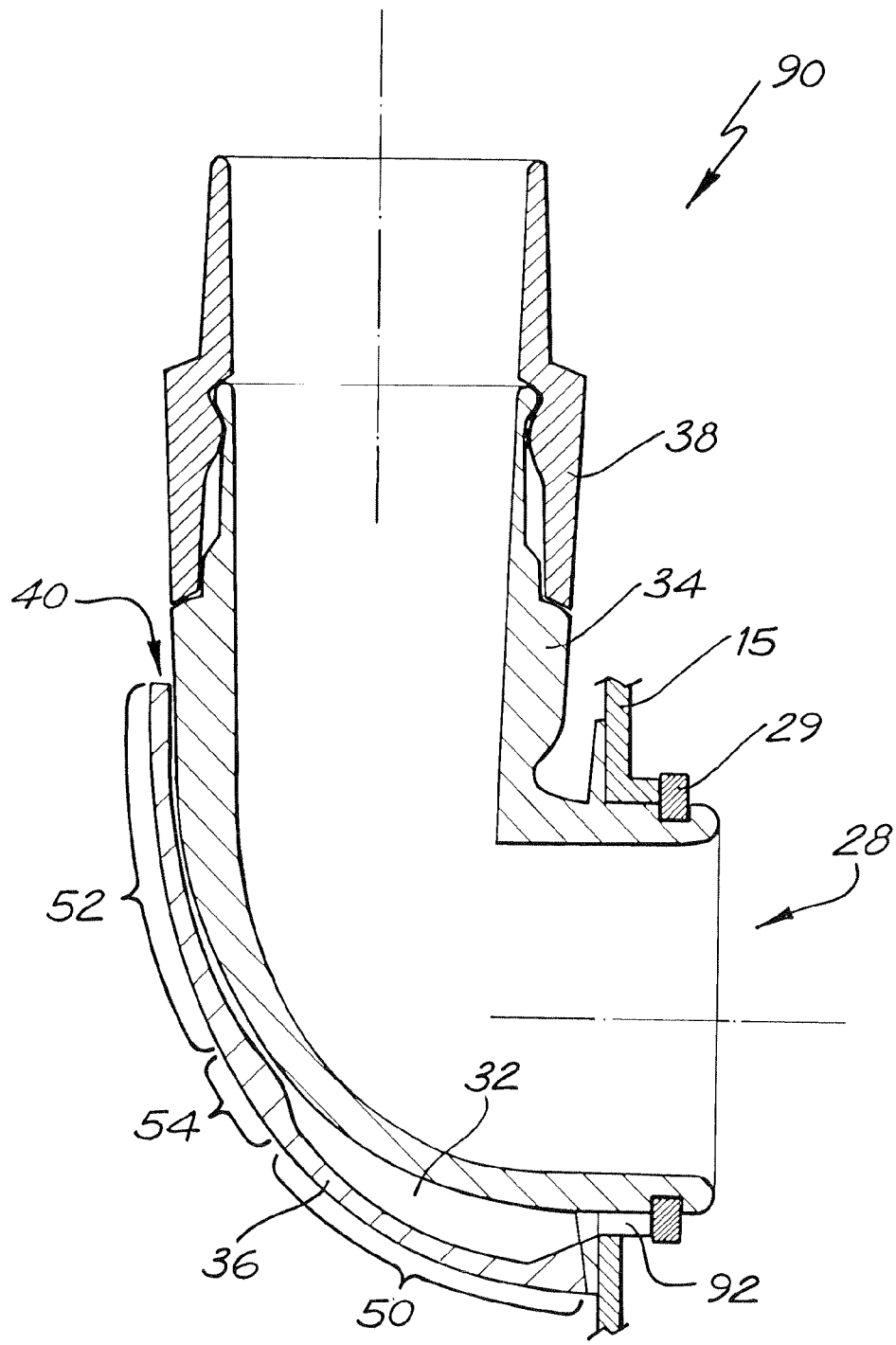
FIG. 7 is a cross-sectional side view of a third embodiment of the connector in accordance with the first aspect of the invention.

FIG. 7 shows a third embodiment of the connector 90 according to the first aspect of the invention. Like reference numerals to those used in describing the first embodiment will again be used to indicate like features in the third embodiment. The connector 90 also has the vent passage 32 in direct fluid communication with the interior of the mask 12. However, in this embodiment, an inlet port 92 is formed in the mask shell 15.

Figure 9:
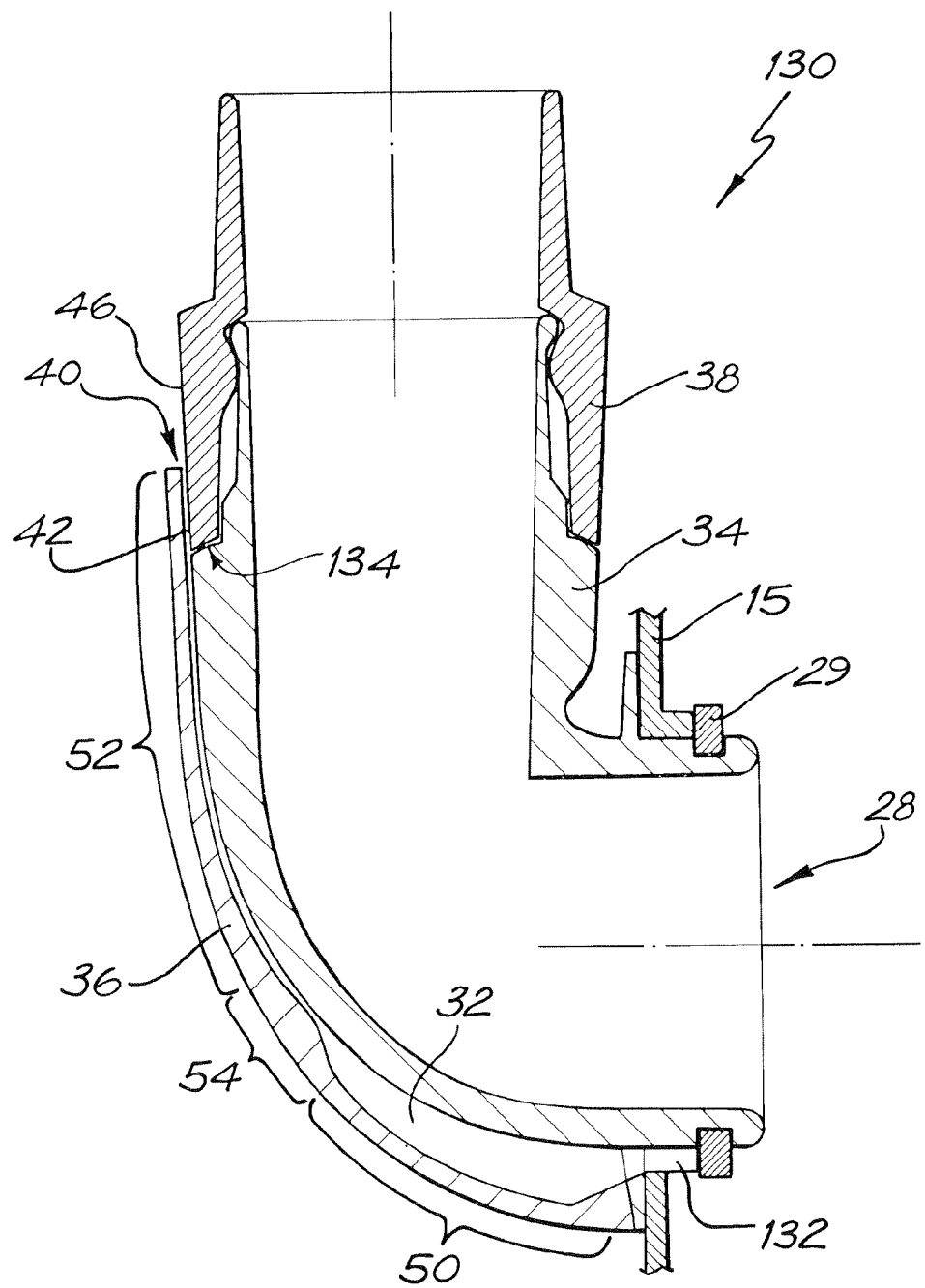
FIG. 9 is a cross-sectional side view of a fourth embodiment of the connector in accordance with the first aspect of the invention

FIG. 9 shows a fourth embodiment of the connector 130 according to the first aspect of the invention. Like reference numerals to those used in describing the first embodiment will again be used to indicate like features in the fourth embodiment. The connector 130 also has an inlet port 132 formed in the mask shell 15, similar to the third embodiment. However, in this embodiment, both the interior surface 42 and the smoothly prolongating adjacent exterior surface 46 are provided on the swivel joiner 38. As the gas vents to the atmosphere downstream of the join 134 between the swivel joiner 38 and the body portion 34, then any gas leaking through the join 134 cannot disturb the flow of gas at, or after, the outlet 40. In this way, a further opportunity for turbulence, and thus noise generation, is eliminated.

Figure 8:
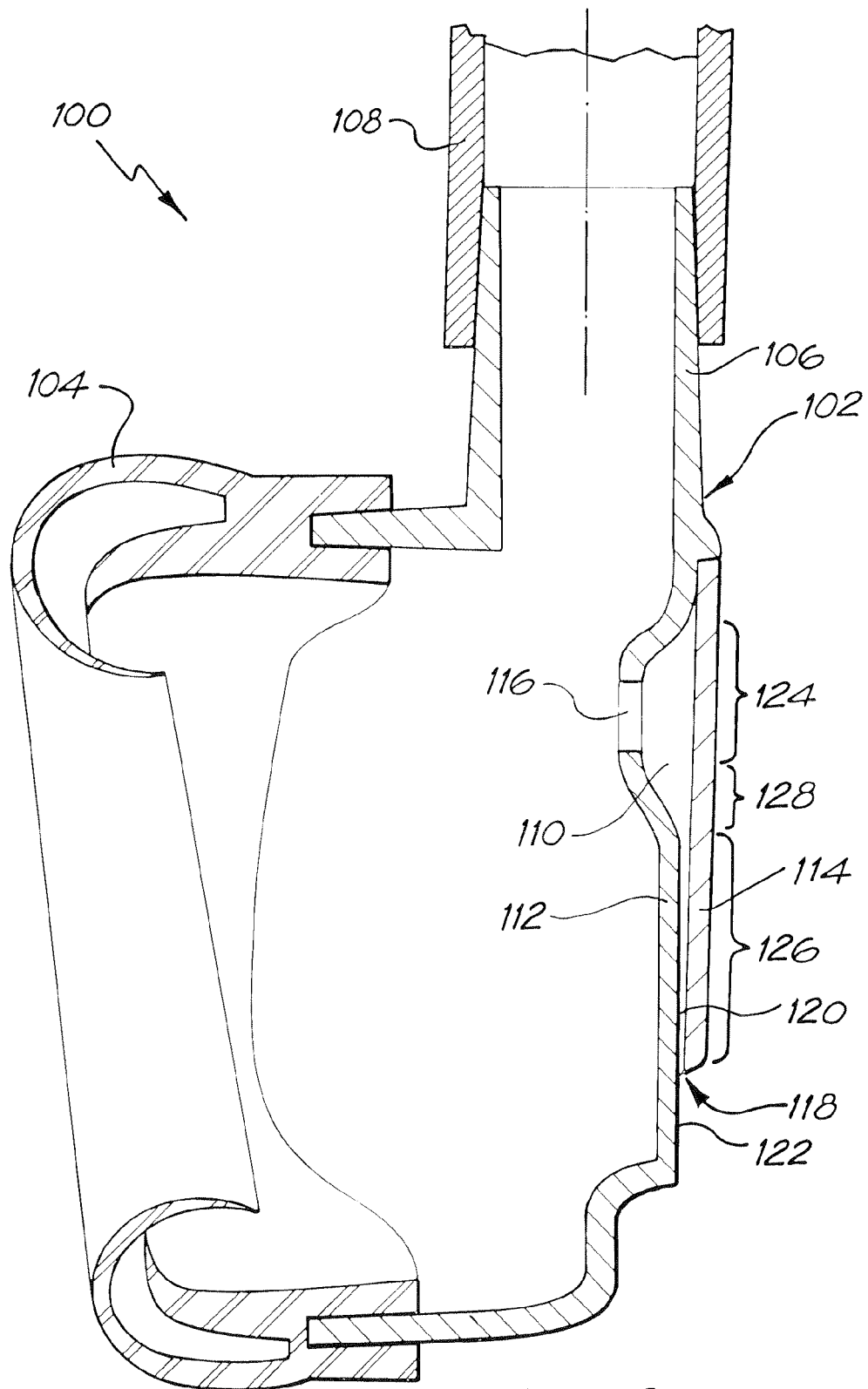
FIG. 8 is a cross-sectional side view of a first embodiment of a respiratory mask in accordance with the second aspect of the invention.

FIG. 8 shows a first embodiment of a nasal respiratory mask 100 in accordance with the second aspect of the invention. The mask 100 includes a mask shell 102 and a mask cushion 104. The mask shell 102 includes a mask inlet 106 for connecting in fluid communication with the outlet of the breathable gas supply conduit 108. The mask 100 includes a gas washout vent passage indicated generally by the reference numeral 110.

The mask shell 102 is comprised of a body portion 112 and a detachable/attachable cap portion 114. The vent passage 110 includes an inlet port 116 formed in the body portion 112 of the mask shell 102. The inlet port 116 is in direct fluid communication with the interior of the mask 100. The vent passage 110 also includes an outlet 118 in fluid communication with the atmosphere. The outlet 118 includes an interior surface 120 on the exterior of the body portion 112 that forms a smooth prolongation with an adjacent surface 122 also provided on the exterior of the body portion 112. The outlet 118 is adapted to direct the washout gas in a direction substantially parallel to the longitudinal axis of the mask inlet 106 and away from the mask inlet 106.

As with earlier embodiments, the noise produced by venting the exhaled gas to the atmosphere is minimized by directing the vented gas on a smooth continuing surface before and after the outlet 118 and away from the mask 100, the patient and other potential disturbances. Additionally, as with the earlier connector embodiments, the cap portion 114 is detachable from the body portion 112 for cleaning and or replacement with a cap portion of same, or different, size or shape. The vent passage 110 also similarly comprises an inlet portion 124 of relatively large cross-sectional area, a relatively long outlet portion 126 of relatively small cross-sectional area and a transition portion 128 of smoothly reducing cross-section extending from the inlet portion 124 to the outlet portion 126.

Although the invention has been described with reference to the preferred embodiments, it will be appreciated by those skilled in the art that the invention may be embodied in many other forms.

We claim:

1. A respiratory mask assembly for delivering breathable gas to a patient, comprising:

a mask main body having a front surface and a rear surface adapted in use to face the patient, the mask main body providing an aperture therethrough for the introduction of breathable gas into a nasal breathing cavity; and an elbow assembly having a generally L shape including a first leg and a second leg, the first leg including a mask end portion swivelably coupled to the front surface of the mask main body and in fluid communication with the aperture, the elbow assembly including a vent passage to allow the passage of exhaust gas from the nasal breathing cavity to atmosphere, wherein the mask end portion of the elbow assembly includes an outlet port for supplying the breathable gas to the nasal breathing cavity and an inlet port of the vent passage for receiving the exhaust gas from the nasal breathing cavity, the outlet port being separated from the inlet port by a dividing wall, the inlet port being arranged to directly oppose the nasal breathing cavity, in use, when the mask end portion is coupled to the front surface of the mask main body.

2. A respiratory mask assembly according to claim 1, wherein the elbow assembly has a surface that is adapted to directly engage a surface of a gas delivery tube.

3. A respiratory mask assembly according to claim 1, wherein the second leg of the elbow assembly includes a swivel connector to connect to a gas delivery tube.

4. A respiratory mask assembly according to claim 1, wherein the mask end portion of the elbow assembly includes a connecting portion that is inserted into the aperture provided in the mask main body and a retaining member is attached to the connecting portion from an inner side of the mask main body so as to prevent withdrawal of the connecting portion from the aperture.

5. A respiratory mask assembly according to claim 1, wherein the dividing wall is configured to direct exhaust gas away from the nasal breathing cavity in a first direction that is substantially opposite to a second direction in which the outlet port delivers incoming gas to the nasal breathing cavity.

6. A respiratory mask assembly according to claim 1, wherein the second leg of the elbow assembly has a first end portion in communication with a gas delivery tube and wherein the mask end portion is detachably coupled to the mask main body.

7. A respiratory mask assembly according to claim 6, wherein the mask end portion of the elbow assembly includes a connecting portion adapted to be inserted into the aperture of the mask main body, and wherein a retaining member is adapted to engage a receiving space in the connecting portion.

8. A respiratory mask assembly according to claim 7, wherein the mask main body includes a flange surrounding the aperture, and the connecting portion extends beyond the flange when the mask end portion is in an operative position.

9. A respiratory mask assembly according to claim 1, further comprising a removable cap portion detachably connected to the elbow assembly, wherein the cap portion includes a main body at least partially defining an outlet for gas washout.

10. A respiratory mask assembly according to claim 1, further comprising a cushion provided to the mask main body.

11. A respiratory mask assembly according to claim 1, wherein the mask main body is a mask shell.

12. A respiratory mask assembly according to claim 1, wherein the vent passage is structured to extend only along a portion of a circumference of the elbow assembly.

13. A respiratory mask assembly according to claim 1, wherein the elbow assembly includes a swivel connector to connect to a gas delivery tube, wherein the mask end portion of the elbow assembly includes a connecting portion that is inserted into the aperture provided in the mask main body and a retaining member that is attached to the connecting portion from an inner side of the mask main body so as to prevent withdrawal of the connecting portion from the aperture, wherein the dividing wall is configured to direct exhaust gas away from the nasal breathing cavity in a first direction that is substantially opposite to a second direction in which the outlet port delivers incoming gas to the nasal breathing cavity, wherein the elbow assembly has a first end portion in communication with the gas delivery tube and wherein the mask end portion is detachably coupled to the mask main body, and wherein the mask main body includes a flange surrounding the aperture, and the connecting portion extends beyond the flange when the mask end portion is in an operative position.

14. A respiratory mask assembly according to claim 13, wherein the retaining member is adapted to engage a groove in the connecting portion.

15. An elbow assembly for a respiratory mask assembly that delivers breathable gas to a patient, the elbow assembly comprising:
   a swivel elbow including a first end portion in communication with a gas delivery tube and a mask end portion configured to be detachably and swivelably coupled to a mask main body to deliver breathable gas to a breathing cavity of the mask assembly,
   the swivel elbow including a vent passage to allow the passage of exhaust gas from the breathing cavity to atmosphere,
   wherein the mask end portion of the swivel elbow includes an outlet port for supplying the breathable gas to the breathing cavity and an inlet port of the vent passage for receiving the exhaust gas from the breathing cavity, the outlet port being separated from the inlet port by a dividing wall,
   wherein the dividing wall is configured to direct exhaust gas away from a breathing cavity in a first direction that is substantially opposite to a second direction in which the outlet port delivers incoming gas to the breathing cavity, and wherein the swivel elbow has a generally L shape including a first leg and a second leg, and the mask end portion is disposed in the first leg.

16. An elbow assembly according to claim 15, further comprising a swivel connector between the swivel elbow and the gas delivery tube.

17. An elbow assembly according to claim 15, wherein the swivel elbow includes a connecting portion that is inserted into an aperture provided in the mask main body and a retaining member is attached to the connecting portion from an inner side of the mask main body so as to prevent withdrawal of the connecting portion from the aperture.

18. An elbow assembly according to claim 15, wherein the mask end portion of the swivel elbow includes a connecting portion adapted to be inserted into an aperture of the mask main body, and wherein a retaining member is adapted to engage a groove in the connecting portion when the mask end portion is in an operative position.

19. An elbow assembly according to claim 15, further comprising a removable cap portion detachably connected to the swivel elbow, wherein the cap portion includes a main body at least partially defining an outlet for gas washout.

20. An elbow assembly according to claim 15, wherein the vent passage includes an outlet, the outlet adapted to be positioned in close proximity to the breathing cavity.

21. An elbow assembly according to claim 15, wherein the outlet port, the inlet port and the dividing wall of the swivel elbow comprise a one-piece structure.

22. An elbow assembly according to claim 15, wherein the vent passage is structured to extend only along a portion of a circumference of the swivel elbow.

23. A respiratory mask assembly for delivering pressurized breathable gas to a patient for Continuous Positive Airway Pressure treatment of a sleep disorder, comprising:
   a mask main body having a front surface and a rear surface adapted to face the patient when the mask assembly is worn, the mask main body providing an aperture therethrough for the introduction of breathable gas into a nasal breathing cavity at least partially formed by the mask main body; and
   an elbow assembly having a generally L shape including a first leg and a second leg, the first leg including a mask end portion swivelably coupled to the front surface of the mask main body and in fluid communication with the aperture, the elbow assembly including a vent passage to allow the passage of exhaust gas from the nasal breathing cavity to atmosphere,
   wherein the mask end portion of the elbow assembly includes an outlet port for supplying the breathable gas to the nasal breathing cavity and an inlet port of the vent passage for receiving the exhaust gas from the nasal breathing cavity, the outlet port being separated from the inlet port by a dividing wall, the inlet port being arranged to directly oppose the nasal breathing cavity, in use, when the mask end portion is coupled to the front surface of the mask main body.

24. A respiratory mask assembly according to claim 23, wherein the nasal breathing cavity is adapted to supply the breathable gas to the patient's airways at a pressure in the range of 3-20 cm $H_2O$.

25. A respiratory mask assembly according to claim 23, wherein the elbow assembly has a surface that is adapted to directly engage a surface of a gas delivery tube.

26. A respiratory mask assembly according to claim 23, wherein the second leg of the elbow assembly includes a swivel connector to connect to a gas delivery tube.

27. A respiratory mask assembly according to claim 23, wherein the mask end portion of the elbow assembly includes a connecting portion that is inserted into the aperture provided in the mask main body and a retaining member is attached to the connecting portion from an inner side of the mask main body so as to prevent withdrawal of the connecting portion from the aperture.

28. A respiratory mask assembly according to claim 23, wherein the dividing wall is configured to direct exhaust gas away from the nasal breathing cavity in a first direction that is substantially opposite to a second direction in which the outlet port delivers incoming gas to the nasal breathing cavity.

29. A respiratory mask assembly according to claim 23, wherein the second leg of the elbow assembly has a first end portion in communication with a gas delivery tube and wherein the mask end portion is detachably coupled to the mask main body.

30. A respiratory mask assembly according to claim 23, wherein the mask end portion of the elbow assembly includes a connecting portion adapted to be inserted into the aperture of the mask main body, and wherein a retaining member is adapted to engage a groove in the connecting portion.

31. A respiratory mask assembly according to claim 23, wherein the elbow assembly includes a swivel connector to connect to a gas delivery tube,
- wherein the mask end portion of the elbow assembly includes a connecting portion that is inserted into the aperture provided in the mask main body and a retaining member that is attached to the connecting portion from an inner side of the mask main body so as to prevent withdrawal of the connecting portion from the aperture,
- wherein the dividing wall is configured to direct exhaust gas away from the nasal breathing cavity in a first direction that is substantially opposite to a second direction in which the outlet port delivers incoming gas to the nasal breathing cavity,
- wherein the elbow assembly has a first end portion in communication with the gas delivery tube and wherein the mask end portion is detachably coupled to the mask main body, and
- wherein the mask main body includes a flange surrounding the aperture, and the connecting portion extends beyond the flange when the mask end portion is in an operative position.

32. A respiratory mask assembly according to claim 31, wherein the retaining member is adapted to engage a groove in the connecting portion.

* * * * *